United States Patent
Biber

(10) Patent No.: US 11,378,675 B2
(45) Date of Patent: Jul. 5, 2022

(54) METHOD AND DEVICE FOR DETECTING MOVEMENT OF A SUBJECT

(71) Applicant: Siemens Healthcare GmbH, Erlangen (DE)

(72) Inventor: Stephan Biber, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/211,009

(22) Filed: Mar. 24, 2021

(65) Prior Publication Data
US 2021/0325525 A1 Oct. 21, 2021

(30) Foreign Application Priority Data
Apr. 17, 2020 (EP) .................................. 20170061

(51) Int. Cl.
*G01S 13/62* (2006.01)
*G01R 33/565* (2006.01)

(52) U.S. Cl.
CPC ........ *G01S 13/62* (2013.01); *G01R 33/56509* (2013.01)

(58) Field of Classification Search
USPC ....................................................... 324/307
See application file for complete search history.

(56) References Cited

U.S. PATENT DOCUMENTS

| | | | |
|---|---|---|---|
| 2009/0267601 A1* | 10/2009 | Van Helvoort .... | G01R 33/3692 324/309 |
| 2014/0070807 A1 | 3/2014 | Biber | |
| 2017/0160367 A1* | 6/2017 | Schroter ............ | G01R 33/3607 |
| 2018/0353140 A1 | 12/2018 | Speier | |
| 2020/0166597 A1* | 5/2020 | Speier .................. | H04B 13/005 |
| 2020/0367765 A1* | 11/2020 | Bacher ................ | A61B 5/7214 |
| 2020/0396112 A1* | 12/2020 | Biber ................. | G01R 33/3607 |

FOREIGN PATENT DOCUMENTS

| | | |
|---|---|---|
| DE | 102012216292 A1 | 5/2014 |
| EP | 3413076 A1 | 12/2018 |

OTHER PUBLICATIONS

European Search Report for European Application No. 20170061.4-1115 dated Oct. 20, 2020.
Speier, P., M. Fenchel, and R. Rehner. "PT-Nav: a novel respiratory navigation method for continuous acquisitions based on modulation of a pilot tone in the MR-receiver." Magn Reson Mater Phys Biol Med 28 (2015): S97-S98.

* cited by examiner

*Primary Examiner* — Rodney E Fuller
(74) *Attorney, Agent, or Firm* — Lempia Summerfield Katz LLC

(57) ABSTRACT

A method for detecting movement of a subject inside a magnetic resonance imaging device includes: providing at least one input signal; using the at least one input signal to generate a higher pilot tone signal having a transmission frequency at least twice as high as the Larmor frequency of the magnetic resonance imaging device; transmitting the higher pilot tone signal towards the subject using a transmitting antenna; receiving the transmitted higher pilot tone signal using a receiving antenna; using the at least one input signal to convert the frequency of the transmitted higher pilot tone signal to an intermediate frequency equal to or lower than the frequency of the input signal; and forwarding the transmitted pilot tone signal to an analysis system to detect changes in the transmitted pilot tone signal caused by movement of the subject.

20 Claims, 2 Drawing Sheets

METHOD AND DEVICE FOR DETECTING MOVEMENT OF A SUBJECT

The present patent document claims the benefit of European Patent Application No. 20170061.4, filed Apr. 17, 2020, which is hereby incorporated by reference in its entirety.

TECHNICAL FIELD

The disclosure relates to a method for detecting movement of a subject, a system for detecting movement of a subject and a local RF coil for a magnetic resonance imaging device configured to detect movement.

BACKGROUND

In magnetic resonance imaging (MRI), it is necessary to avoid or at least detect the movement of the subject or patient being imaged, over the whole time of the image acquisition. Movement of the subject may lead to artefacts, which increase the difficulty of interpretation of the image, to incorrect medical findings and/or may require the repetition of the image acquisition process. The extremities are sometimes fixated within the local RF coil to suppress movement, but for the head such fixation is less acceptable for most patients. For some imaging processes, it is important to detect the movement caused by the heartbeat or breathing, for example, to trigger the image acquisition accordingly.

Prior art approaches have attempted to gain information about movement by inducing radio frequency (RF) signals which are close to but outside the frequency band of the RF signals used for the MR imaging (e.g., the Larmor frequency). These RF signals are called pilot tone (PT) signals, and the method was first disclosed in Peter Speier et al. "*PT-Nav: A Novel Respiratory Navigation Method for Continuous Acquisition based on Modulation of a Pilot Tone in the MR receiver*". ESMRMB, 129: 97-98, 2015. doi: 10.1007/s10334-015-0487-2. The frequency of the pilot tone signal lies outside the frequency band of the MRI system to avoid mutual interference; however, it is close enough that it may be transmitted and processed by the RF coil and further equipment used to transmit and process the magnetic resonance signal. Approaches using the pilot tone have been focused on the application in context of breathing and heartbeat. However, a further problem is the movement of other body parts of the subject, e.g., movement of the head or movement of extremities, including knees, hands, or feet.

In the pilot tone method, the frequency of the pilot tone signal has to be close to the frequency of the MR-signal because a signal has to be received with an existing narrow-banded local RF coil. Furthermore, the existing signal processing system may not be configured to also operate at significantly higher frequencies. This leads to frequencies smaller than 130 MHz at magnetic fields of 3 Tesla or less. Interaction with tissue, in particular human tissue, is quite weak in this frequency range. Most of the effect of the pilot tone method is caused by change of eddy currents in the tissue. This effect is weak due to a low conductivity of tissue at a frequency of about 100 MHz. Furthermore, due to the long wavelengths, there are only near field effects and hardly any standing waves or reflection effects.

Another approach to detect movement during an MR acquisition is to attach optical markers to the subject, which are tracked by cameras. For example, a so-called "Kinetic Sensor" includes an in-bore, real-time patient viewing system, allowing close patient monitoring and prospective motion correction for neurological MRI exams. However, this approach requires the installation of additional hardware (e.g., cameras), as well as an additional act of attaching the markers to the subject. Moreover, it is not always possible to allow for an unhindered view of the cameras onto the subject. While this solution might lead to quite exact results, a method which requires lower efforts and expenses would be desirable.

SUMMARY AND DESCRIPTION

It is therefore an object of the disclosure to provide a method and related system which is able to efficiently and accurately detect movement of a subject or patient being imaged in a magnetic resonance imaging device.

The scope of the present disclosure is defined solely by the appended claims and is not affected to any degree by the statements within this summary. The present embodiments may obviate one or more of the drawbacks or limitations in the related art.

According to a first aspect, a method is provided for detecting movement of a subject located inside a magnetic resonance imaging (MRI) device. The method includes: providing at least one input signal; using the at least one input signal to generate a higher pilot tone signal having a transmission frequency which is at least twice as high as the Larmor frequency of the magnetic resonance imaging device; transmitting the higher pilot tone signal towards the subject using a transmitting antenna, the transmitted higher pilot tone signal interacting with the subject; receiving the transmitted higher pilot tone signal using a receiving antenna; using the at least one input signal to convert the frequency of the transmitted higher pilot tone signal to an intermediate frequency which is equal to or lower than the frequency of the or at least one of the at least one input signal, thereby generating a transmitted pilot tone signal; and forwarding the transmitted pilot tone signal to an analysis system to detect changes in the transmitted pilot tone signal caused by movement of the subject.

The subject may be a human or animal, (e.g., a patient to be imaged in a magnetic resonance device). The subject is located inside an MRI device, meaning that at least a part of its body is located inside the sensitive area of such MRI device, for example, inside the bore of a main magnet. In some embodiments, the part of the body to be imaged is further inside the sensitive area of a local RF coil, in particular an RF coil which is to be placed close to the part of the body from which images are to be acquired. The part of the body may be the head, a part of an extremity such as a knee, leg, or part thereof, foot, arm, hand etc. Alternatively, the part of the body may be the thorax and/or abdomen, or the part of the body may be an organ such as the heart, pulmonary system, liver, kidney, etc. The local RF coil may be of any type, it may be a head coil, knee coil, or a flexible array coil used for imaging of abdomen or thorax. However, the method may also be used without local coil, e.g., the MR signal may be acquired by the body coil fixedly integrated in the MRI device.

The MRI device may be a commercially available medical MRI device, wherein the method may advantageously be used with any existing device. For example, the MRI device may use a main magnetic field strength of 0.5-3 Tesla, corresponding to a Larmor frequency in a range of about 20 MHz and 130 MHz. The Larmor frequency may be in a range of about 40 and 90 MHz, corresponding to about 1 to 2 Tesla. In some embodiments, the MRI device may operate at different Larmor frequencies, either because the MRI device may acquire signals from various chemical elements, or because the main magnetic field may be changed. In most embodiments, the Larmor frequency refers to the frequency of the MRI signal used for the MRI acquisition (e.g., imaging or spectroscopy) of the subject inside the MRI device, which may be the Larmor frequency of hydrogen.

The method allows detection of movements of the subject, in particular of the body part located inside the sensitive area of the MRI device, and in particular of the local RF coil. A detected movement may be a natural and unavoidable movement caused, for example, by breathing or heartbeat, but also voluntary and involuntary movements of the subject or its body parts caused by anxiety or impatience, such as a head or extremities. In most embodiments, the method allows detection of whether a movement, or a movement sufficient to disturb the MRI measurement, has taken place. In most embodiments, the method does not allow to trace the movement, e.g., to detect how much and in which direction such movement has taken place. One purpose of the disclosure is to detect whether movement has taken place, and when such movement has been detected, further measures may be taken, e.g., the MRI acquisition may be repeated, or the MRI acquisition may be interrupted, and an MRI navigator image may be taken in order to correct further measurements.

In an embodiment, the method is carried out while Magnetic Resonance (MR) measurements of the subject are taking place using the MRI device, such as MR imaging of spectroscopy.

The at least one input signal may be any periodic oscillating electronic signal, (e.g., a sine wave or a square wave), or it may be based on such a signal, for example, a modulated signal. It may be pulsed or continuous. The input signal may be produced by a frequency generator or local oscillator, which may be a crystal oscillator, optionally stabilized by a phase locked loop (PLL), an oven-controlled crystal oscillator (OXCO), or a direct digital synthesizer (DDS). Such electronic oscillator may be placed outside the sensitive area of the MRI system, in particular outside the bore of the main MR magnet, for example, in a space outside a Faraday cage enclosing the main MR magnet and RF coils.

The disclosure may make use of at least one input signal, e.g., a local oscillator (LO) signal, which is provided to a local RF coil in presently available MR architectures, for example, the LO signal is provided at the interface of the MR system to which the local RF coils is connected during an MR acquisition, e.g., using a connector. The frequency conversions disclosed herein (e.g., the generating of a higher pilot tone signal and/or the converting of the frequency of the higher pilot tone signal to an intermediate frequency) may be carried out on board of the local RF coil, or within separate transmitting and receiving devices which may be attached to any local RF coil.

The frequency conversions may be carried out using analogue signals, because the high transmission frequency is easier to generate in analogue than digitally. However, in certain embodiments, the output signal (e.g., transmitted pilot tone signal) will eventually be digitalized, in particular, by sampling with a pre-determined sampling frequency which may be in a range of 1 and 30 MHz, in a range of 5 and 20 MHz, or in a range of 8 and 12 MHz.

The frequency of the at least one input signal(s) may lie in the range of 5 MHz to 1,000 MHz, in the range of 10 MHz to 500 MHz, or in the range of 50 MHz to 150 MHz. According to an embodiment, the at least one input signal includes at least one local oscillator signal. In certain embodiments, there are at least two different input signals, in particular, at least two input signals having different frequencies. By mixing different signals having different frequencies, signals having a variety of frequencies may be generated. In an embodiment, one input signal is an information-carrying (e.g., modulated) signal, and at least one further input signal is local oscillator signal providing a certain frequency. For example, the input signals may include a local oscillator signal and a pilot tone signal as described below, but the disclosure may also be carried out with a single input signal.

The input signal is used to generate a higher pilot tone signal having a transmission frequency which may be higher than the frequency of the input signal. For example, the transmission frequency may be a multiple of the frequency of the input signal. In case of several input signals, the frequency of the higher pilot tone signal may be a combination of the frequencies of the input signals, and which may be generated by frequency multiplication and/or frequency division and/or mixing. At least some or all frequency multiplication, division, and/or mixing acts may be followed by a band-pass filtering act, in order to let pass the signal components within the desired frequency range, e.g., the frequency range which is to be obtained by the frequency multiplication and/or frequency dividing or mixing act. In certain embodiments, frequency multiplication entails that harmonics are generated having a frequency of n times the input frequency, where n is an integer (n=1, 2, 3, . . . ). Frequency division may entail that the frequency is divided by an integer, (e.g., by an exponential of 2, such as 2 to the power of m, where m is an integer). Thus, for example, the frequency of the input signal may be multiplied by a factor n, where n=1, ½, ¼, ⅛, 1/16, . . . . The frequency of the higher pilot tone signal is termed the transmission frequency because it is the frequency at which the signal is radiated towards the subject or patient, and thus radio waves at this higher frequency interact with the subject.

The transmission frequency is at least twice as high as the Larmor frequency at which MR measurements are made. Therefore, the method has the advantage over the pilot tone method that higher frequencies are used, and thereby the interaction with body tissue is significantly improved. At such higher frequency, the signal variations caused by movement of the patient will be higher by an order of magnitude than the signal variations which may be observed in current pilot tone methods. Movement of the subject may lead to change of the eddy currents, which in turn may change the transmitted higher pilot tone signal, e.g., a change of the amplitude or the phase of the signal may be induced. Advantageously, the higher frequency of the transmitted higher pilot tone signal with respect to a prior art pilot tone signal leads to stronger interactions with the tissue and, therefore, to a more significant change of the signal of up to about one order of magnitude. This is due to an increased conductivity of the tissue at higher frequencies leading to a stronger interaction. Therefore, movement may be detected more easily and more precisely.

The transmission frequency may be significantly higher than the Larmor frequency, for example, 2 to 128 times as high, 4 to 64 times as high, or 8 to 32 times as high. For example, the transmission frequency may be 300 MHz or higher, e.g., in a range of 300 MHz and 20 GHz, in a range of 400 MHz and 10 GHz, or in a range of 600 MHz and 6 GHz. In an embodiment, the frequency of the transmitted higher pilot tone signal lies in the range of ISM radio bands. This may simplify or render unnecessary the licensing of a corresponding system used for applying this method. It may also help to avoid interference with other signals or other medical equipment.

The higher pilot tone signal is then transmitted towards the subject, whereby the electronic signal may be converted into a radio signal, which is radiated towards the subject via a transmitting antenna. Therefore, the transmitted higher pilot tone signal may be considered to be a radio-based signal. Interacting with the subject means that the transmitted higher pilot tone signal is, for example, interacting with tissue of the subject, e.g., via eddy currents in the subject's tissue. The radiated (e.g., transmitted) higher pilot tone signal is then received by a receiving antenna, in particular a transmission signal is received.

The transmitting antenna and the receiving antenna are configured to be used in the desired frequency range, e.g., in the frequency range of the transmitted pilot tone signal. Advantageously, these antennas are able to transmit and receive higher frequencies than the pre-existing equipment in MRI-systems. In other words, in most embodiments the transmitting and receiving antennas are not RF coils used for transmitting the MR signal, but separate antennas. For example, such transmitting and receiving antennas may be attached to a local RF coil, in particular a head coil, or a local RF coil that for the knee, spine, wrist or breast. It is also conceivable that the antennas are connected to flexible anterior coils for imaging the abdomen or the cardiovascular system. The transmitting and receiving antennas may also be disposed somewhere else within or close to the sensitive area of the MRI device, for example, the antennas may be attached to the inside of the magnet Bore. In order to be sensitive to movement of the body parts being currently examined, the antennas may be less than 500 mm or less than 300 mm away from such body parts. The additionally required electronics and/or the antennas for transmitting and/or receiving may be implemented in an area of about $5 \times 5$ cm$^2$. Such antennas and the required electronics may be provided separately and, e.g., attached to existing local RF coils, or may be placed close to the subject's body by other means, for example, by attaching it to the inside of the bore of the main MR magnet. Alternatively, such additional antennas and electronics may be integrated into the MRI device, or into local RF coils.

After receiving by the receiving antenna, the frequency of the transmitted higher pilot tone signal is converted to an intermediate frequency, which is equal to or lower than the frequency of the or one of the input signal(s), whereby a so-called transmitted pilot tone signal, also referred to as output signal, is generated at such intermediate frequency. Thereby, the signal is easier to process with the existing electronic components. Furthermore, the relatively low frequency of the input signal(s) (e.g., the local oscillator) and of the output signal facilitates the handling of the connecting cables, and there will be less interference at lower frequency between the cables.

The conversion of the transmitted higher pilot tone signal may be carried out using frequency mixing with the at least one input signal, or with signal(s) generated from the at least one input signal, e.g., by frequency multiplication or frequency division, wherein a mixing act may be followed by band-pass filter.

Converting the frequency to a frequency which is even lower than the input signal(s) makes it even easier to process the signal (e.g., by converting it from analogue to digital, amplifying it etc.) and transfer it to an analysis system. The analysis system may be any digital processing system, for example, it may be part of the control computer of the MRI system. The analysis system may be realized by any processing unit, (e.g., a CPU), and may be on any computer or laptop or tablet. It is also conceivable to transmit the signal via a local area network or wireless LAN to a remotely located analysis system.

The analysis system may then detect changes in the transmitted pilot tone signal and thereby deduce the movement of the subject. According to an embodiment, a movement of the subject is detected if the frequency and/or phase and/or amplitude of the transmitted pilot tone signal changes beyond a pre-determined threshold. In this embodiment, the higher pilot tone signal may be a continuous signal of constant frequency, and the transmitted pilot tone signal is observed for changes in itself, e.g., over time, such as by constantly monitoring frequency, phase, and/or amplitude, (e.g., only frequency and/or phase), and observing if they change, e.g., by at least a pre-determined threshold within a pre-determined time window. Alternatively, the transmitted pilot tone signal (e.g., output signal) may be compared with the input signal from which the higher pilot tone signal was generated, to thereby detect any changes above a pre-determined threshold.

Whenever a movement of the subject has thus been detected, according to an embodiment, the analysis system may register that such movement has taken place, and use such information, e.g., to disregard any data acquired after such movement, or to re-start the current image acquisition process. Alternatively, the new position may be captured, e.g., by measuring the new position of the subject using an MR navigator and adjusting the scan axes of the current image acquisition protocol accordingly by translation and/or rotation.

According to an embodiment, the at least one input signal includes at least one local oscillator signal and a pilot tone signal. The at least one local oscillator signal may be used to convert the frequency of the pilot tone signal to the transmission frequency, thereby generating the higher pilot tone signal.

The at least one local oscillator signal may be any periodic oscillating electronic signal, for example, a sine wave or a square wave, which may be provided by an electronic oscillator. The pilot tone signal may also be a periodic oscillating electronic signal. In an embodiment, the frequency of the pilot tone signal is close to the Larmor frequency of the MRI-system. For example, at a magnetic field of 1.5 tesla, the frequency of the pilot tone may be around 63.5 MHz. This allows to advantageously use already existing electronic components. In particular, a pilot tone signal is used, which is already incorporated in an existing MRI system. This minimizes the costs as the amount of additional electronic components and connections is lower. More generally, the pilot tone signal may have a frequency in a range of 10 MHz to 500 MHz or in the range of 50 MHz to 150 MHz. It may be modulated signal (as opposed to a constant sine wave).

According to an embodiment, the act of converting the frequency of the pilot tone signal to the transmission frequency and/or the act of converting the transmitted higher pilot tone signal include mixing the respective signal with the at least one input signal, in particular with a local oscillator (LO) signal or a frequency-multiplied or frequency-divided local oscillator signal having a carrier frequency. The carrier frequency may be generated by frequency multiplication of the LO signal by an integer, or by frequency division by an integer, (e.g., by 2 to the power of n, where n is an integer, such than the frequency may be multiplied by 1, ½, ¼, ⅛, ¹⁄₁₆, etc.). When mixing two signals, multiplicative mixing may be applied, in particular frequency mixing, wherein the frequency of the local oscillator signal or of the frequency-multiplied local oscillator signal is added to the frequency of the pilot tone signal to generate the higher pilot tone signal. The processing of the transmitted higher pilot tone signal on the other hand may involve subtracting the frequency of the local oscillator signal or the frequency of the multiplied local oscillator signal from the frequency of the transmitted higher pilot tone signal. A bandpass filter may be applied after the act of mixing the pilot tone signal or the transmitted higher pilot tone signal with the at least one local oscillator signal or a frequency multiplied local oscillator signal to filter the desired harmonics or products of intermodulation. By adding a multiplied local oscillator signal, even higher frequencies may be achieved, thereby further increasing the interference with the tissue of the subject.

Advantageously, using the at least one local oscillator signal to convert the pilot tone signal up to a higher frequency as well as to convert the transmitted higher pilot tone signal down to a frequency which is equal to the pilot tone signal makes it easier to process, (e.g., sample), as well as analyze the pilot tone signal. In an embodiment, the same local oscillator signal may be used in the generating of a higher pilot tone signal and/or the converting of the frequency of the higher pilot tone signal to an intermediate frequency, thereby only needing one signal processing chain for the local oscillator signal.

In useful embodiments, the frequency of the pilot tone signal is multiplied or divided prior to mixing it with the local oscillator signal or frequency-multiplied local oscillator signal. Multiplying the frequency of the pilot tone signal constitutes an alternative and/or additional way of achieving higher frequencies. Furthermore, a low frequency input signal may be used as pilot tone signal. For example, the frequency of the pilot tone signal may be significantly lower than the Larmor frequency of the MRI system, (e.g., in the range of 8 to 12 MHz). Or the frequency of the pilot tone signal may be similar or equal to the Larmor frequency, while the multiplied pilot tone signal is twice or three times or many times the Larmor frequency.

According to a further embodiment, the frequency of the higher pilot tone signal is a combination of the frequencies of the at least one local oscillator signal and the pilot tone signal. The frequency of the higher pilot tone signal may thus be created by adding the frequency of the pilot tone signal multiplied or divided by a pre-determined integer, and the frequency of at least one local oscillator signal multiplied or divided by another pre-determined integer. Optionally, one or several more local oscillator signals with a frequency that is multiplied or divided by yet another pre-determined integer may be also added in order to create the higher pilot tone signal. This might, for example, lead to a frequency $f_{HPT}$ of the higher pilot tone signal with respect to the frequencies of the pilot tone signal $f_{PT}$, a first local oscillator signal $f_{LO1}$ and a second local oscillator signal $f_{LO2}$ in the form:

$$f_{HPT} = N_0 f_{PT} + N_1 f_{LO1} + N_2 f_{LO2},$$

where $N_0$, $N_1$, $N_2$ are integers, (e.g., exponentials of base 2). In certain embodiments, these integers may be in a range of 0 and 256, in a range of 0 and 64, or in a range of 8 and 32. In useful embodiments, $N_2$ is zero, (e.g., only one local oscillator signal is required). In some embodiments, $N_0 = 1$.

According to an embodiment, the act of generating a higher pilot tone signal includes multiplying (and/or dividing) the frequency of the at least one local oscillator signal to obtain a multiplied local oscillator signal and mixing the multiplied local oscillator signal with the pilot tone signal, thereby obtaining the higher pilot tone signal. Multiplying the signal may be achieved with a frequency multiplier, thereby allowing for transmitted higher pilot tone signals with frequencies that are considerably higher than the frequencies of the input signals, e.g., the frequency of the pilot tone signal and the frequency of the local oscillator signal. This enables a higher flexibility during the measurement of movement of the subject. Furthermore, it is possible to adjust the frequency to the respective requirements, of the measurement, for example, to measure different parts of a subject which may be composed of different materials, or to focus on objects within the subject at different depths.

According to an embodiment, the act of converting the transmitted higher pilot tone signal to a lower intermediate frequency includes the act of mixing the transmitted higher pilot tone signal with the at least one local oscillator signal or a frequency multiplied local oscillator signal down to the frequency of the pilot tone signal to obtain a transmitted pilot tone signal, and optionally mixing the transmitted pilot tone signal down to an intermediate frequency below the frequency of the pilot tone signal. It may also include an act of frequency division, as described above. Mixing the signal down a second time creates even lower frequencies, which further simplifies the signal processing. The frequency below the frequency of the pilot tone signal may be in the range of 5 to 30 MHz, in the range of 5 to 15 MHz, or in the range of 8 to 12 MHz.

According to an embodiment, the pilot tone signal is a modulated signal having a frequency close to or equal to the Larmor frequency of the magnetic resonance imaging device (e.g., a frequency within the bandwidth of the receiving antenna, such as within 5 MHz of the Larmor frequency). Using the pilot tone signal or the frequency which is close to or equal to the Larmor frequency makes it possible to easily incorporate this method with existing systems like the Siemens Sola/Vida® systems where local oscillator signals and pilot tone signals are already available.

According to a further embodiment, the transmitting antenna and the receiving antenna are disposed at a local RF coil which is placed in the proximity of a body part of the subject. Disposing the antennas at a local RF coil makes it easier to implement the method in existing systems by simply updating existing local RF coils or using new local RF coils that are already equipped with the corresponding antennas.

According to a further embodiment, the transmitted higher pilot tone signal has a transmission frequency that is higher than 300 MHz or higher than 600 MHz. The higher frequency may increase interference of the signal with the subject, in particular with the tissue of a body. Higher frequencies may increase the interference and therefore the observable change of the transmitted pilot tone signal, thereby making it easier to detect movement of the subject, and it is thus desirable to utilize high frequencies. On the other hand, higher frequencies will make signal processing more difficult. This problem is at least partially circumvented by the up and down mixing of the pilot tone signal.

According to a further embodiment, the method is carried out simultaneously using a first transmitting antenna transmitting at a first transmission frequency and a corresponding first receiving antenna, and a second transmitting antenna transmitting at a second transmission frequency and a corresponding second receiving antenna. Using two or more transmitting and receiving antennas makes it possible to detect movement of several parts of the subject at once and/or to observe one part of a subject from different angles at once. The transmitting antennas and/or the receiving antennas may be either located close to each other, for example, several antennas might be attached to one local RF coil or they may be located at different locations, e.g., at different local RF coils. For example, it is conceivable to detect the movement of different parts of the subject at once, by placing antennas at different locations, and/or to detect the movement of the same part of the subject from different angles, thus, e.g., facilitating detecting movement in different directions.

In certain embodiments, first and second transmission frequencies differ by more than 100 MHz to 20 GHz, by more than 500 MHz to 10 GHz, or by more than 1 to 5 MHz. Utilizing frequencies that are far apart from each other makes it possible to focus on different objects of the subject which are located at different depths at the subject. Depending on the corresponding depths of the different objects and also of the properties of the subject at this location concerning the penetration of radiation, different frequencies and also different intervals between the frequencies may be appropriate. In an alternative embodiment, first and second transmission frequencies may be close to each other, for example, they might differ by less than 100 MHz, (e.g., in a range of 10 and 80 MHz). Frequencies that are different, but close to each other, make it possible to observe a part of the subject from different directions without different signals interfering with each other, using different antennas that are sensitive to different frequencies or by applying a bandpass filter, which lets pass only the corresponding frequency of the signal that is supposed to be received by this antenna. Thus, it may be made sure that different signals may be distinguished.

According to an alternative embodiment, the higher pilot tone signal is transmitted in the form of a frequency modulated continuous wave (FMCW). For example, by varying up and down the frequency over a certain period of time, the frequency difference between a transmitted signal and a reflected received signal makes it possible to determine a distance via the frequency difference between the transmitted signal and the received signal. By continuously observing the distance, movement will be detected. In an alternative embodiment, the higher pilot tone signal is transmitted in the form of a pulse radar. Thereby, a pulse is transmitted, and time is measured until the pulses are reflected back to the receiving antenna, thereby enabling a measurement of the distance and, by comparing consecutive pulses, the measurement of movement as well.

According to another aspect, the disclosure provides a system for detecting movement of a subject located inside a magnetic resonance imaging device. The system includes an interface configured to receive at least input signal, in particular at least one local oscillator signal and a pilot tone signal. The system further includes a multiplier and/or divider and/or a first mixer that is/are configured to use the at least one input signal to generate a higher pilot tone signal having a transmission frequency which is at least twice as high as the Larmor frequency of the magnetic resonance imaging device, in particular by using at least one local oscillator signal to convert the frequency of a pilot tone signal to the transmission frequency. The system further includes a transmitting antenna configured to transmit the higher pilot tone signal. The system further includes a receiving antenna configured to receive the transmitted higher pilot tone signal. The system further includes a second mixer configured to use the at least one input signal, (in particular the local oscillator signal), to convert the frequency of the transmitted higher pilot tone signal to an intermediate frequency equal to or lower than the frequency of the or at least one of the input signals, (in particular lower than the frequency of the pilot tone signal or the at least one local oscillator signal), to thereby generated a transmitted pilot tone signal (also referred to as output signal). The system further includes an interface configured to forward the transmitted pilot tone signal.

All features of the method may be configured to the system and vice versa. The interface configured to receive a signal and the interface configured to forward the signal may optionally both be part of one input/output interface.

According to an embodiment, the system is part of a local RF coil or the system is configured to be part of a local RF coil or to be an additional part attached to the outside of a local RF coil. Specifically, the transmitting antenna and/or the receiving antenna may be part of the local RF coil or configured to be part of the local RF coil or to be an additional part attached to the outside of the local RF coil.

According to an embodiment, the interface configured to receive the input signal(s), (e.g., the at least one local oscillator signal and a pilot tone signal), a first multiplier, the first mixer, and the transmitting antenna may be part of the local RF coil, or configured to be an additional part, which may be attachable to the local RF coil or elsewhere. Also, the receiving antenna, a second multiplier, the second mixer, and an interface configured to forward the transmitted pilot tone signal may be part of the local RF coil or may be configured to be an additional part, which may be attachable to the local RF coil or elsewhere. The components which are not part of the local RF coil may be attached or attachable to a bore of the MRI system. This may, on the one hand, allow to save space on the corresponding local RF coil. On the other hand, it may enable the system to observe the subject and thereby detect its movement from additional different angles through sending the transmitted higher pilot tone signal towards the subject from another/alternative position.

According to another aspect, the disclosure provides a local RF coil for a magnetic resonance imaging device, the local RF coil being configured to detect movement of a part of a subject's body located in proximity thereto. The local RF coil includes one or several coil elements configured to transmit a magnetic resonance signal. The local RF coil further includes a coil connector configured to receive at least one input signal, in particular a local oscillator signal and a pilot tone signal. The local RF coil further includes at least one system for detecting movement of a subject according to any one of the embodiments of the systems described herein.

Providing a local RF coil with a system for detecting movement, facilitates updating existing MRI systems with the movement detection system by simply adding and/or replacing and/or updating corresponding local RF coils. Updating existing local RF coils is particularly advantageous because it might require only small changes accompanied by only small costs, especially if the existing local RF coils and or the existing MRI system already include the provision of a pilot tone signal and/or of one or several local oscillator signals.

BRIEF DESCRIPTION OF THE DRAWINGS

Embodiments of the disclosure are now described with reference to the attached figures.

DETAILED DESCRIPTION

Figure 1:
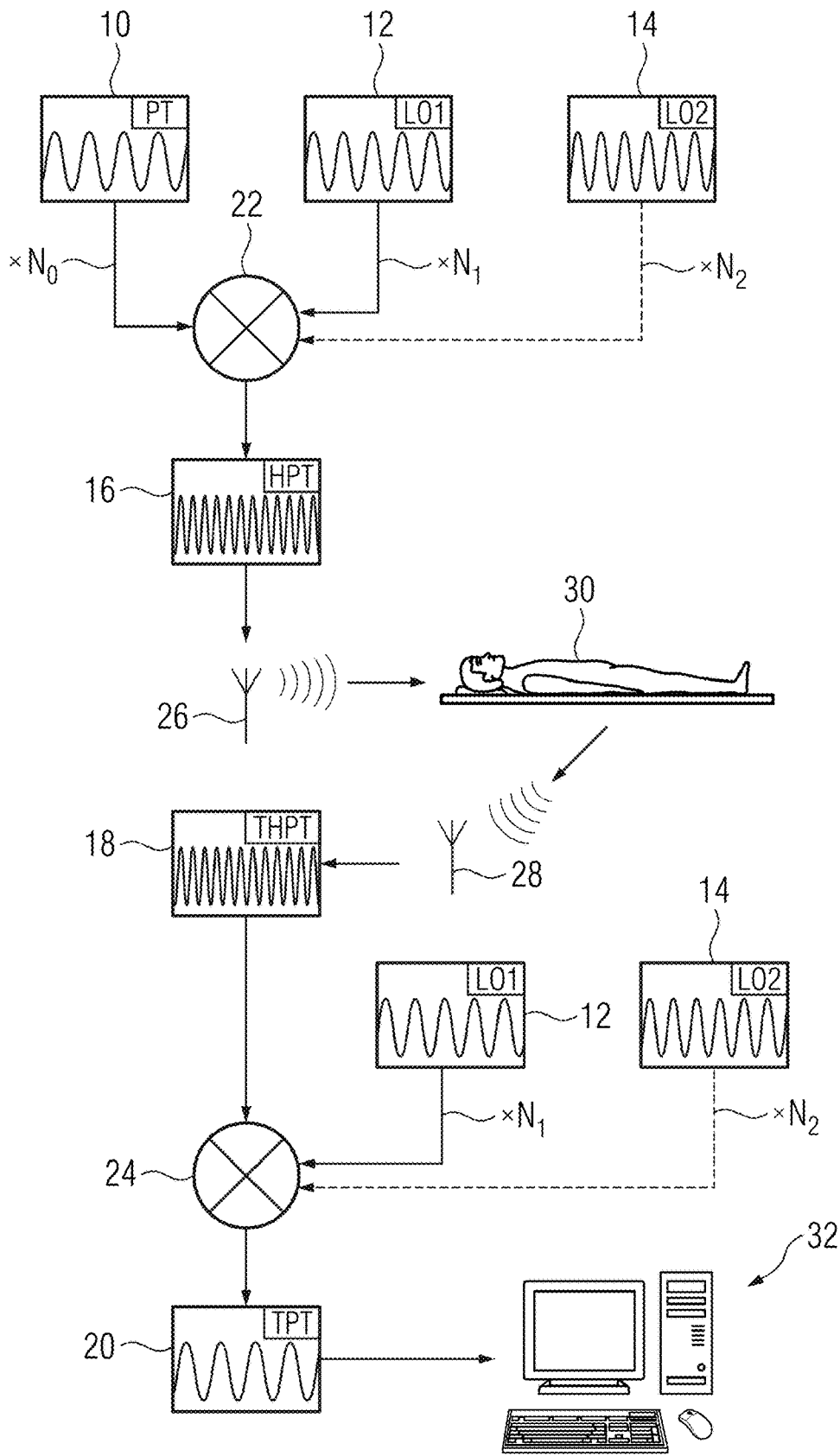
FIG. 1 depicts a schematic flow diagram illustrating an embodiment of a method for detecting movement of a subject.

FIG. 1 depicts an embodiment of a method for detecting movement of a subject 30. In this embodiment, a pilot tone (PT) signal 10 is provided. Furthermore, a first local oscillator signal LO1 12 and a second local oscillator signal LO2 14 are provided. The frequency of the pilot tone signal 10 may be multiplied by a factor $N_0$. The frequency of the local oscillator signal 12 may be multiplied by a factor $N_1$ and the frequency of the second local oscillator signal 14 may be multiplied by a factor $N_2$, $N_0$, $N_1$ and $N_2$ being integers. Alternatively, or additionally to the frequency multiplication, frequency division may be applied. In a next act, the frequencies of the pilot tone signal 10, the local oscillator signal 12 and, optionally, the second local oscillator signal 14 are added with a first mixer 22 to result in a higher pilot tone signal 16, which has a frequency, which is the sum of the frequencies of the (e.g., multiplied) pilot tone signal 10, the (e.g., multiplied) local oscillator signal 12 and, optionally, the (e.g., multiplied) second local oscillator signal 14.

The higher pilot tone signal 16 is transmitted via an antenna 26 towards the subject 30, (e.g., a patient). After interacting with the patient 30, the transmitted higher pilot tone signal 18 is received by a receiving antenna 28. By using a second mixer 24, the frequency of the local oscillator signal 12 multiplied by the same integer $N_1$ and optionally the frequency of the second local oscillator signal 14 multiplied with the integer $N_2$ are subtracted from the frequency of the transmitted higher pilot tone signal 18, leading to a transmitted pilot tone signal 20, which has the same frequency as the original pilot tone signal 10. In an additional act, the transmitted pilot tone signal 20 is then forwarded to an analysis system 32, which in this case is a computer. The computer may then be used to detect changes in the transmitted pilot tone signal 20 and trace these changes back to movement of the patient 30.

Figure 2:
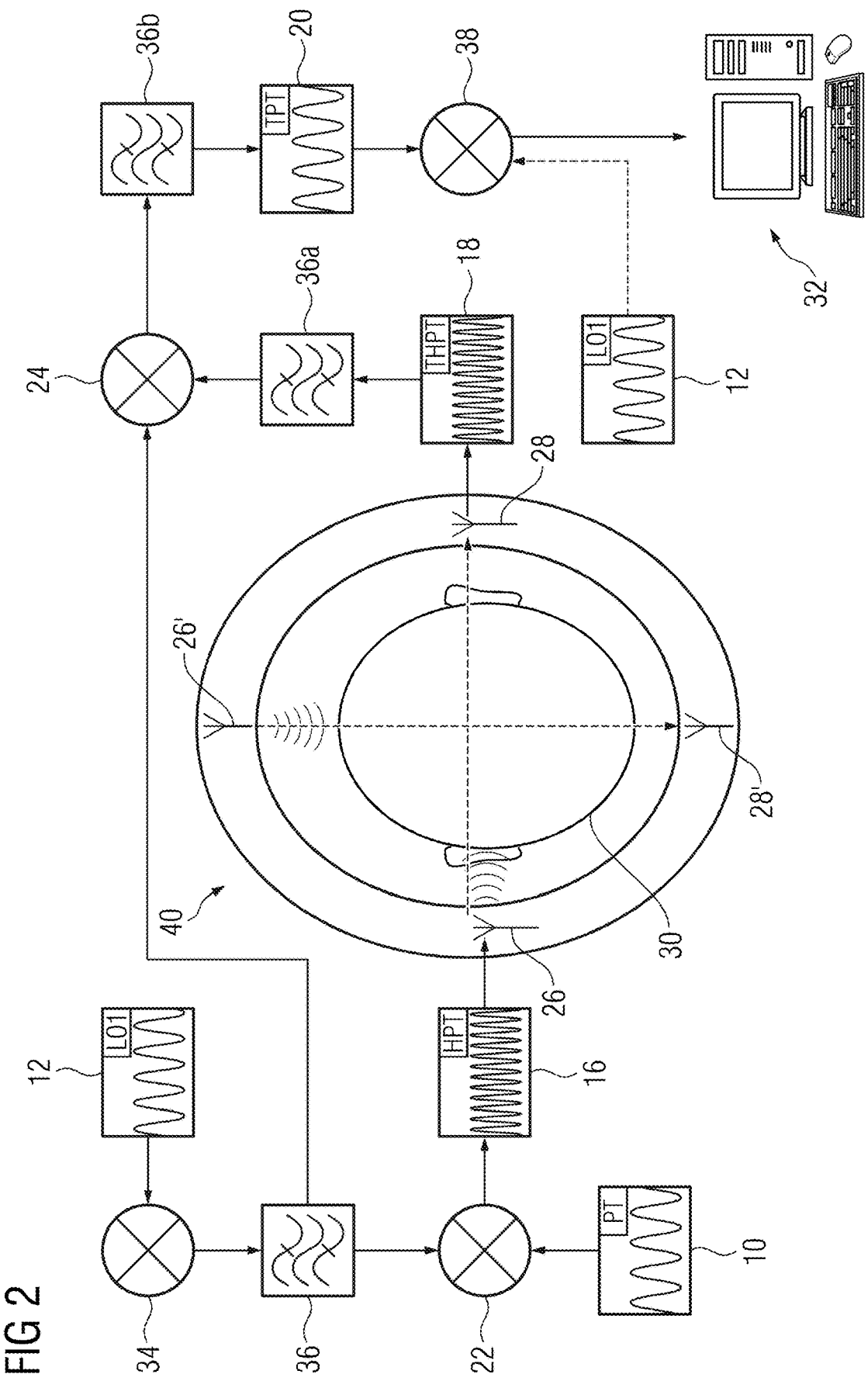
FIG. 2 depicts a schematic cross-section of a local RF coil for an MRI device, with a system for detecting movement of a subject according to an embodiment.

FIG. 2 depicts an embodiment of a local RF coil 40 for an MRI device with a system for detecting movement of a subject, the body part being a patient's head 30 in this case. The head 30, shown in an axial cross-sectional view, is located inside a head coil 40. The system is configured to receive a local oscillator LO1 signal 12 and a pilot tone PT signal 10. For example, the LO1 signal is generated by an oscillator (e.g., a PLL stabilized quartz or an OXCO) which is phase-locked to the local oscillator signal provided to the local RF coil. The frequency of the LO1 may be 75 MHz, and the LO1 signal is frequency-multiplied by multiplier/divider 34, to, e.g., reach a frequency of 600 MHZ ($N_1$=8). The multiplier/divider 34 may include diodes and/or transistors, or a digital gate, as known in the art. The multiplication and/or division 34 is followed by a bandpass filter 36 to filter the desired harmonics to obtain a multiplied and/or divided local oscillator signal.

Furthermore, the system includes a first mixer 22, (e.g., a multiplicative mixer), which mixes the multiplied local oscillator signal with the pilot tone signal 10. In some embodiments, the mixer includes or is followed by band pass filter which suppresses the undesired side bands and lets pass the signal in the desired transmission frequency range, (e.g., a certain linear combination, such as the sum), of the multiplied frequency of the local oscillator signal 12 (600 MHz) and the frequency of the pilot tone signal 10 (63.5 MHz), e.g., 663.5 MHz, thereby generating a higher pilot tone signal 16. The system further includes a transmitting antenna 26 attached to inside of the local RF coil 40, wherein the transmitting antenna 26 is configured to transmit the higher pilot tone signal 16 towards a patient's head 30. Additionally, the system includes a receiving antenna 28 configured to receive the transmitted higher pilot tone signal THPT 18. The THPT 18 is first filtered by another bandpass filter 36a in order to eliminate any noise, and optionally pre-amplified by a pre-amplifier (not shown). The received THPT signal 18 is then mixed at second mixer 24 with the multiplied and filtered local oscillator signal having a frequency $N_1 * f_{LO}$=600 MHz. The second mixer 24 is followed by a third bandpass filter 36b configured to filter the desired frequency of the transmitted pilot tone signal 20, which is this case is $f_{THPT} - N_1 * f_{LO}$=663.5 MHz–600 MHz=63.5 MHz. In other words, the frequency of the multiplied local oscillator signal 12 is subtracted from the frequency of the transmitted higher pilot tone signal 18, thereby generating the transmitted pilot tone signal 20 having a frequency that is about equal to the frequency of the pilot tone signal 10, (e.g., 63.5 MHz). This signal 20 is further mixed by a third mixer 38, again using the first local oscillator LO1 signal 12 at 75 MHz, to thereby generate an output signal at about 12 MHz, which may be sampled at for example 10 MHz in an analog-to-digital converter (ADC) (not shown). The resulting signal may then be forwarded over an interface towards an analysis system 32, which is a computer in this case.

In addition to the transmitting antenna 26 and the receiving antenna 28, the local RF coil 40 also includes a second transmitting antenna 26' and a second receiving antenna 28'. The second transmitting antenna 26' and the second receiving antenna 28' are connected to a signal processing system (not shown here), which is equivalent to the signal processing system in which the transmitting antenna 26 and the receiving antenna 28 are connected. The two transmission reception systems allow for observation of the patient's head 30 from two different angles, or at two different depths. For example, it is possible to transmit different frequencies which are close together, (e.g., 600+63.5 MHz and 600+2× 63.5 MHz), e.g., the pilot tone signal PT is multiplied before mixing with the multiplied LO1 signal. Alternatively, the signals transmitted by the two antennas 26 and 26' may be far apart, for example, at one of the frequencies (in MHz) 600+63.5, 1200+63.5, 2400+63.5 and 4800+63.5. In other words, the integer number $N_1$ by which the signal LO1 is multiplied may be an exponential of base 2 and may be in a range of 4 and 124, (e.g., one of 8, 16, 32, and 64).

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been illustrated and described in detail with the exemplary embodiments, the disclosure is not restricted by the examples disclosed and other variations may be derived therefrom by a person skilled in the art without departing from the protective scope of the disclosure.

The invention claimed is:

1. A method for detecting movement of a subject located inside a magnetic resonance imaging device, the method comprising:
   providing at least one input signal;
   generating, using the at least one input signal, a higher pilot tone signal having a transmission frequency at least twice as high as a Larmor frequency of the magnetic resonance imaging device;
   transmitting the higher pilot tone signal towards the subject using a transmitting antenna, wherein the transmitted higher pilot tone signal interacts with the subject;
   receiving the transmitted higher pilot tone signal using a receiving antenna;
   converting, using the at least one input signal, the transmission frequency of the transmitted higher pilot tone signal to an intermediate frequency equal to or lower than a frequency of the at least one input signal, thereby generating a transmitted pilot tone signal; and
   forwarding the transmitted pilot tone signal to an analysis system to detect changes in the transmitted higher pilot tone signal caused by movement of the subject.

2. The method of claim 1, wherein the at least one input signal comprises at least one local oscillator signal and a pilot tone signal, and
   wherein the at least one local oscillator signal is used to convert a frequency of the pilot tone signal to the transmission frequency, thereby generating the higher pilot tone signal.

3. The method of claim 2, wherein the transmission frequency of the higher pilot tone signal is a combination of the frequency of the at least one local oscillator signal and the frequency of the pilot tone signal.

4. The method of claim 3, wherein the converting of the frequency of the pilot tone signal and/or the converting of the transmitted higher pilot tone signal comprise mixing the respective signal with the at least one local oscillator signal or a frequency-multiplied local oscillator signal having a carrier frequency.

5. The method of claim 4, wherein the generating of the higher pilot tone signal comprises:
   multiplying or dividing a frequency of the at least one local oscillator signal to obtain a multiplied or divided local oscillator signal; and
   mixing the multiplied or divided local oscillator signal with the pilot tone signal, thereby obtaining the higher pilot tone signal.

6. The method of claim 5, wherein the converting of the transmitted higher pilot tone signal to the intermediate frequency comprises:
   mixing the transmitted higher pilot tone signal with the at least one local oscillator signal or a frequency-multiplied local oscillator signal down to the frequency of the pilot tone signal to obtain the transmitted pilot tone signal.

7. The method of claim 6, wherein the converting of the transmitted higher pilot tone signal to the intermediate frequency further comprises:
   mixing the transmitted pilot tone signal down to an intermediate frequency below the frequency of the pilot tone signal.

8. The method of claim 2, wherein the converting of the frequency of the pilot tone signal and/or the converting of the transmitted higher pilot tone signal comprise mixing the respective signal with the at least one local oscillator signal or a frequency-multiplied local oscillator signal having a carrier frequency.

9. The method of claim 2, wherein the generating of the higher pilot tone signal comprises:
   multiplying or dividing a frequency of the at least one local oscillator signal to obtain a multiplied or divided local oscillator signal; and
   mixing the multiplied or divided local oscillator signal with the pilot tone signal, thereby obtaining the higher pilot tone signal.

10. The method of claim 2, wherein the converting of the transmitted higher pilot tone signal to the intermediate frequency comprises:
    mixing the transmitted higher pilot tone signal with the at least one local oscillator signal or a frequency-multiplied local oscillator signal down to the frequency of the pilot tone signal to obtain the transmitted pilot tone signal.

11. The method of claim 10, wherein the converting of the transmitted higher pilot tone signal to the intermediate frequency further comprises:
    mixing the transmitted pilot tone signal down to an intermediate frequency below the frequency of the pilot tone signal.

12. The method of claim 1, wherein the pilot tone signal is a modulated signal having a frequency equal to or within 5 MHz of the Larmor frequency of the magnetic resonance imaging device.

13. The method of claim 1, wherein the transmitting antenna and the receiving antenna are disposed at a local RF coil placed in a proximity of a body part of the subject.

14. The method of claim 1, wherein the transmitted higher pilot tone signal has a transmission frequency that is higher than 300 MHz.

15. The method of claim 1, wherein the method is carried out simultaneously using a first transmitting antenna transmitting at a first transmission frequency and a corresponding first receiving antenna, and a second transmitting antenna transmitting at a second transmission frequency and a corresponding second receiving antenna.

16. The method of claim 15, wherein first and second transmission frequencies differ by more than 100 MHz.

17. The method of claim 1, wherein the higher pilot tone signal is transmitted in a form of a frequency modulated continuous wave.

18. A system for detecting movement of a subject located inside a magnetic resonance imaging device, the system comprising:
    an interface configured to receive at least one input signal;
    a multiplier and/or divider and/or a first mixer configured to use the at least one input signal to generate a higher pilot tone signal having a transmission frequency at least twice as high as a Larmor frequency of the magnetic resonance imaging device;
    a transmitting antenna configured to transmit the higher pilot tone signal;
    a receiving antenna configured to receive the transmitted higher pilot tone signal;
    a second mixer configured to use the at least one input signal to convert the transmission frequency of the transmitted higher pilot tone signal to an intermediate frequency equal to or lower than a frequency of the at least one input signal, thereby generating a transmitted pilot tone signal; and
    an interface configured to forward the transmitted pilot tone signal.

19. A system of claim 18, wherein the system is part of a local radio frequency (RF) coil, or
wherein the system is an additional part configured to be attached to the local RF coil.

20. A local radio frequency (RF) coil for a magnetic resonance imaging device, the local RF coil configured to detect movement of a part of a body of a subject located in proximity thereto, the local RF coil comprising:
- at least one coil element configured to transmit a magnetic resonance signal;
- a coil connector configured to receive at least one input signal, wherein the at least one input signal comprises an oscillator signal and a pilot tone signal; and
- a system for detecting movement of a subject, wherein the system comprises:
  - an interface configured to receive at least one input signal;
  - a multiplier and/or divider and/or a first mixer configured to use the at least one input signal to generate a higher pilot tone signal having a transmission frequency at least twice as high as a Larmor frequency of the magnetic resonance imaging device;
  - a transmitting antenna configured to transmit the higher pilot tone signal;
  - a receiving antenna configured to receive the transmitted higher pilot tone signal;
  - a second mixer configured to use the at least one input signal to convert the transmission frequency of the transmitted higher pilot tone signal to an intermediate frequency equal to or lower than a frequency of the at least one input signal, thereby generating a transmitted pilot tone signal; and
- an interface configured to forward the transmitted pilot tone signal.

* * * * *